(12) United States Patent
Beller et al.

(10) Patent No.: US 10,105,156 B2
(45) Date of Patent: Oct. 23, 2018

(54) MULTIFUNCTIONAL INSTRUMENT

(71) Applicant: ERBE ELEKTROMEDIZIN GMBH, Tuebingen (DE)

(72) Inventors: Juergen Beller, Gomaringen (DE); Peter Selig, Nehren (DE); Melanie Veit, Moessingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 738 days.

(21) Appl. No.: 14/508,095

(22) Filed: Oct. 7, 2014

(65) Prior Publication Data

US 2015/0100054 A1 Apr. 9, 2015

(30) Foreign Application Priority Data

Oct. 8, 2013 (EP) ..................................... 13187651

(51) Int. Cl.
*A61B 17/17* (2006.01)
*A61B 17/32* (2006.01)
(Continued)

(52) U.S. Cl.
CPC .......... *A61B 17/32* (2013.01); *A61B 17/3203* (2013.01); *A61B 18/14* (2013.01); *A61B 18/1402* (2013.01); *A61B 2017/00225* (2013.01); *A61B 2018/00589* (2013.01); *A61B 2018/00601* (2013.01); *A61B 2018/00994* (2013.01); *A61B 2018/044* (2013.01); *A61B 2018/046* (2013.01); *A61B 2018/048* (2013.01); *A61B 2018/1425* (2013.01)

(58) Field of Classification Search
CPC ..... A61B 17/32; A61B 18/1402; A61B 18/14; A61B 17/3203; A61B 2018/1425; A61B 2018/00994; A61B 2018/044; A61B 2018/046; A61B 2018/048; A61B 2018/00601; A61B 2017/00225; A61B 2018/00589
See application file for complete search history.

(56) References Cited

U.S. PATENT DOCUMENTS 5,505,729 A 4/1996 Rau
5,609,151 A 3/1997 Muller et al.
(Continued)

FOREIGN PATENT DOCUMENTS

CN 101983038 A 3/2011
EP 2 641 556 A1 9/2013
(Continued)

*Primary Examiner* — Rex R Holmes
(74) *Attorney, Agent, or Firm* — Blank Rome LLP

(57) ABSTRACT

A multifunctional instrument for HF surgical treatment of tissue, in particular for optional cutting, injecting and coagulating tissue is proposed. The multifunctional instrument has the following elements: at least one fluid chamber for receiving a fluid; a temperature control device communicating with said at least one fluid chamber for warming, heating or evaporating a fluid present in said fluid chamber; a temperature controller for controlling the temperature of the fluid present in the said fluid chamber, and at least one fluid outlet port arranged at a distal end of the multifunctional instrument and communicating with the said at least one fluid chamber.

13 Claims, 3 Drawing Sheets

(51) Int. Cl.
*A61B 17/3203* (2006.01)
*A61B 18/14* (2006.01)
*A61B 18/00* (2006.01)
*A61B 17/00* (2006.01)
*A61B 18/04* (2006.01)

(56) References Cited

U.S. PATENT DOCUMENTS

| | | | |
|---|---|---|---|
| 6,270,493 B1 | 8/2001 | Lalonde et al. | |
| 6,328,735 B1* | 12/2001 | Curley | A61B 18/04 606/14 |
| 2003/0097126 A1* | 5/2003 | Woloszko | A61B 18/12 606/41 |
| 2006/0161101 A1* | 7/2006 | Dimalanta | A61B 50/13 604/67 |
| 2007/0112342 A1 | 5/2007 | Pearson et al. | |
| 2009/0125009 A1 | 5/2009 | Zikorus et al. | |
| 2011/0022041 A1 | 1/2011 | Ingle et al. | |
| 2011/0028887 A1 | 2/2011 | Fischer et al. | |
| 2011/0224667 A1 | 9/2011 | Koblish et al. | |
| 2012/0265190 A1* | 10/2012 | Curley | A61B 18/082 606/28 |
| 2013/0030545 A1 | 1/2013 | Gross et al. | |

FOREIGN PATENT DOCUMENTS

| | | |
|---|---|---|
| JP | H5-337125 A | 12/1993 |
| JP | H9-224951 A | 9/1997 |
| JP | 2003-505117 A | 2/2003 |
| JP | 2011-516131 A | 5/2011 |
| JP | 2011/527202 | 10/2011 |
| JP | 2011-527202 A | 10/2011 |
| WO | WO 00/59386 A1 | 10/2000 |
| WO | WO 2009/121563 A2 | 10/2009 |

* cited by examiner

MULTIFUNCTIONAL INSTRUMENT

TECHNICAL FIELD

Embodiments described herein relate to a multifunctional instrument for high frequency (HF) surgical treatment of tissue.

BACKGROUND

Instruments for HF surgical treatment of tissue are well-known in principle. The problem in this case is frequently undesirable side-effects which can result due to the current flow through the patient's tissue, particularly in the relevant operating region. These undesirable side-effects occur particularly during large-area, superficial procedures such as argon plasma coagulation (APC) or spray coagulation. The high voltages used there, which may be up to 4500 V, can cause malfunctions in electronic peripheral devices due to electromagnetic fields in the operating environment. Among other things, they may have adverse effects on patient monitoring, such as on the ECG. During minimally invasive procedures, it is also necessary to use an endoscopic or laparoscopic camera, the image of which can be adversely affected by the high voltage and the electromagnetic fields this generates as a result. It is therefore necessary to use highly insulating materials to shield the appropriate devices in order to prevent the associated interference.

Carbonization effects of the treated tissue and neuromuscular stimulations which are induced by the HF current are another disadvantage of conventional HF surgical procedures. Finally, another disadvantage of conventional HF surgical instruments is the necessity of carrying out an instrument change for different HF surgical treatment steps such as cutting, injecting or coagulating tissue which hampers the surgical procedure. It should also be possible to carry out thermal tissue treatment by means of HF surgical coagulation with maximum tissue conservation. This includes reducing the coagulation depth while simultaneously increasing the surface extension of the coagulation region.

An object of embodiments of the present invention is therefore to create a multifunctional instrument which requires no instrument change for different treatment steps and which moreover prevents side-effects such as interference with peripheral devices, carbonization effects and neuromuscular stimulations.

SUMMARY

A multifunctional instrument is proposed for achieving the object referred to above. The multifunctional instrument according to embodiments of the present invention is used, among other things, for HF surgical treatment of tissue, in particular for optional cutting, injecting and coagulating tissue. According to at least some embodiments disclosed herein, the multifunctional instrument has the following elements: at least one fluid chamber for receiving a fluid; a temperature control device communicating with the at least one fluid chamber for warming, heating or evaporating a fluid present in said at least one fluid chamber; a temperature controller for controlling the temperature of the fluid present in said at least one fluid chamber, and at least one fluid outlet port arranged at a distal end of the multifunctional instrument and communicating with said at least one fluid chamber.

An essential point of embodiments of the invention is, therefore, that the present multifunctional instrument can use a fluid not only for cutting and injecting tissue with a targeted water jet, but also that in addition the fluid can be warmed, in particular heated and even evaporated. Thus the vapor can produce a superficial thermal effect with low penetration depth during coagulation and the treated tissue can be devitalized over a large area. This minimizes the carbonization effects. It is also possible as a result to carry out coagulation of the tissue using a lower voltage such that interference with the peripheral devices present in the operating theatre is prevented. Unlike with conventional APC or spray coagulation procedures, the coagulation depth is lower due to the vapor generated, and the planar extension of the coagulation effect is higher. As a result of the temperature control device integrated in the instrument and the associated temperature controller, the fluid in the fluid chamber can be warmed, heated or evaporated directly at the site of the operation and can therefore be flexibly adjusted to each application as required.

It is particularly advantageous if the temperature control device comprises at least two temperature control electrodes arranged at a distance from each other which, in certain areas at least, form a wall of the fluid chamber. In this case it may be provided that the temperature control electrodes arranged in pairs have a radial gap between them which is determined in particular by at least one preferably annular-shaped spacer. In other words, the at least two temperature control electrodes are preferably arranged at the same height in the axial direction but are at a distance from the insulation in the radial direction. The spacers may be omitted if the temperature control electrodes are attached on an inner surface of a sheath which is in particular cylindrical and flexible and said electrodes are preferably configured in the form of a coating, film or other thin material layer.

Thus, in this embodiment, the temperature control electrodes may also be attached flexibly to a sheath such that the flexibility of the sheath is not compromised, particularly for using the multifunctional instrument as a laparoscopic or endoscopic instrument. It may be further provided that several pairs of temperature control electrodes are provided in the axial direction of the multifunctional instrument's sheath and are attached, in particular segment-like, on the inner surface of said sheath. This prevents that a continuous electrode surface in the axial direction of the sheath breaks during bending of the sheath and in this way prevents a current flow from being interrupted.

To control the temperature of the fluid located in the fluid chamber, the temperature controller can adjust the wattage supplied to the temperature control device, in particular to the temperature control electrodes, as a function of a specified fluid flow rate. It is possible in this way to specify the temperature of the fluid without additional sensors using the flow rate known to the HF surgical device and the wattage supplied. In this case, the temperature difference corresponds to the quotient from the energy supplied and the heat capacity according to the following formula: $\Delta T = \Delta E/(c*m)$.

Also especially preferred is a multifunctional instrument in which the at least one fluid outlet port is arranged in an active electrode configured in the form of a wave guide which protrudes in particular beyond a distal end of a sheath. The wave-guide-shaped active electrode is preferably cylindrical. The proximal end of the active electrode preferably extends into the fluid chamber to prevent water in liquid form from entering the wave-guide-shaped electrode during vapor generation. In this way, drops of evaporated fluid do not collect in the distal region between the active electrode and the wall of the fluid chamber so that the liquid cannot escape through the wave-guide-shaped active electrode. The diameter of the at least one fluid chamber is preferably larger than the diameter of the active electrode in order to create a sufficiently large collection space for non-evaporated fluid at the distal end of the fluid chamber.

Provided that the distal end of the active electrode protrudes beyond a distal end of a sheath of the multifunctional instrument, the active electrode can be used in an advantageous manner both as a mechanical cutting instrument and also as a coagulation electrode. To be able to operate the temperature control electrodes separately from the active electrode, both types of electrodes are preferably equipped with separate connections to the supply cable of a high-frequency current of one or a plurality of HF generators. It is also particularly advantageous if the distal end of the active electrode is configured as a cutting tool for mechanically cutting tissue. In particular, it is envisaged here that the distal end of the active electrode has a cutting edge or the same cutting instrument for mechanical cutting.

A multifunctional instrument according to embodiments of the present invention that has not just one single but rather two or more fluid outlet ports which are arranged at the distal end of the multifunctional instrument is particularly advantageous. The one or a plurality of fluid outlet ports may in this case communicate with a single fluid chamber or with a plurality of fluid chambers that are separate from each other. In particular, the at least one and every further fluid outlet port may be configured as a nozzle-type axial through-hole in an instrument attachment connected to the sheath at the distal end of the instrument. In this manner, the multifunctional instrument can discharge not only a directed jet of water but also, at the same time or alternatively, vapor. The through-holes, in particular in the instrument attachment at the distal end of the multifunctional instrument, may be positioned symmetrically or asymmetrically and in particular centrally or eccentrically. For example, it may be provided to arrange the active electrode with the at least one fluid outlet port centrally in the instrument attachment, while one or a plurality of further fluid outlet ports are arranged eccentrically around the active electrode's fluid outlet port. In the case of more than two fluid outlet ports, a concentric arrangement may be provided in particular around a central fluid outlet port in the vicinity of the active electrode.

A suitable valve unit may be provided to control the fluid discharge out of the one or a plurality of fluid outlet ports, particularly as a function of the fluid or vapor pressure prevailing in the fluid chamber. The valve unit may be configured, for example, as a passive ball or active piezo valve. In this way, the fluid outlet ports which are connected to a single fluid chamber can be operated, and in particular can be opened and closed, arbitrarily according to the application so that the multifunctional instrument can be used for many different applications. In this case, the valve unit is preferably arranged at a proximal end of the fluid outlet port, in particular at a proximal end of the instrument attachment. Alternatively, it may be provided that two different water feed lines, which are separate from each other, and therefore two fluid chambers, which are separate from each other, are provided, their fluid flow being controlled independently of each other, and a separate fluid outlet port being assigned to each fluid chamber. In this case, for example, a fluid chamber may be provided for supplying a focused jet of water for water jet cutting while a further fluid chamber serves to supply liquid for vapor generation during a coagulation procedure.

An HF surgical system is also proposed for achieving the object referred to above. Embodiments of the surgical system has an HF generator for generating a high-frequency treatment current as well as for generating a temperature control current and also comprises a multifunctional instrument.

DETAILED DESCRIPTION

Figure 1:
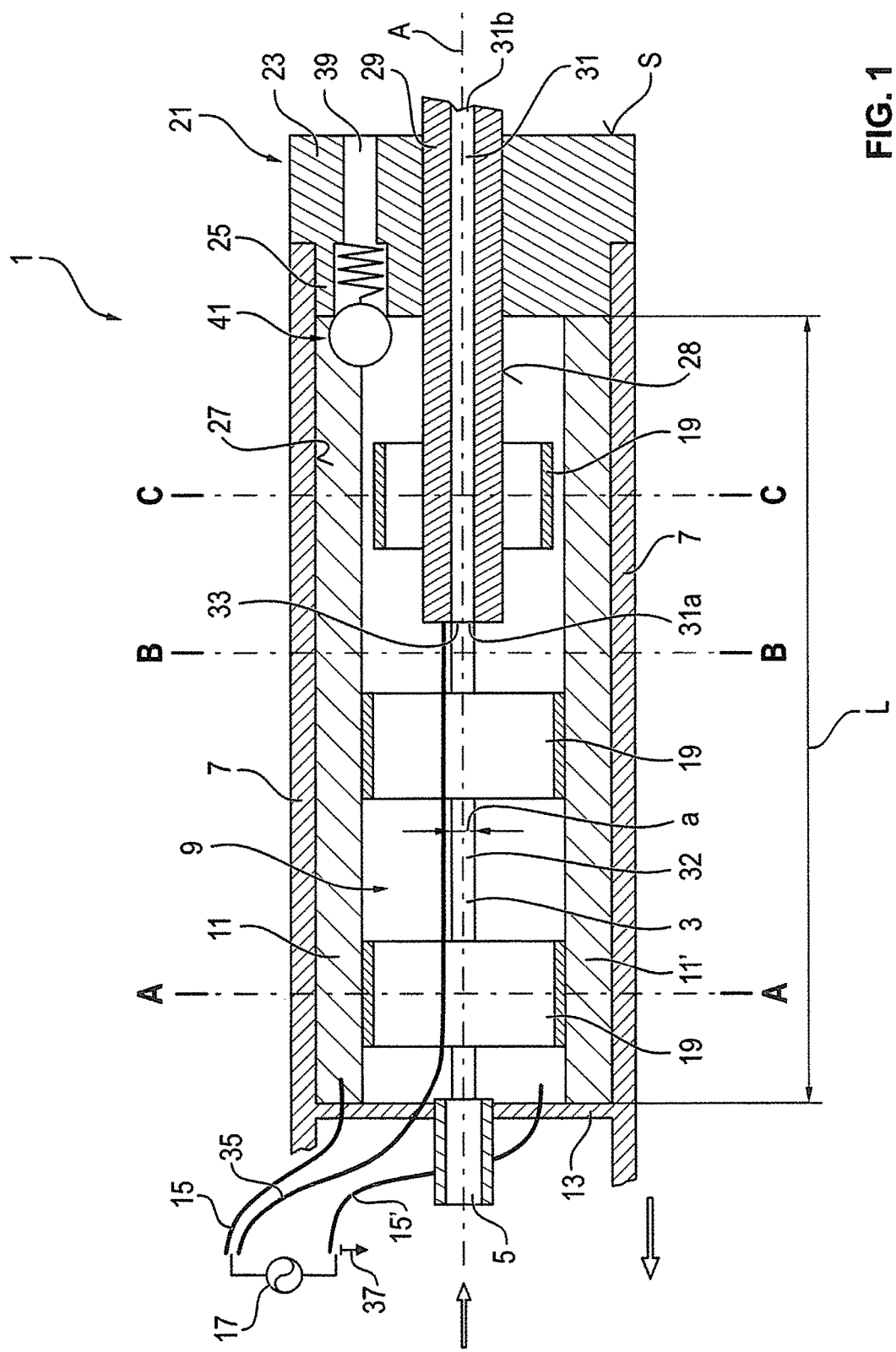
FIG. 1 is a schematic sectional view of a multifunctional instrument according to one embodiment of the present invention.

FIG. 1 shows a schematic sectional view of a multifunctional instrument 1 according to an embodiment of the invention. The multifunctional instrument 1 comprises a fluid chamber 3 for receiving a fluid suitable for treating the human body, for example water or a physiological saline solution (0.9% NaCl). The fluid arrives in the fluid chamber 3 via a fluid inlet 5.

The multifunctional instrument 1 further comprises a sheath 7 which surrounds the fluid chamber 3. In addition, a temperature control device 9 is provided in the form of temperature control electrodes 11, 11' arranged in pairs which, at least in certain areas, form the wall of the fluid chamber 3. In the axial direction A of the multifunctional instrument 1, the fluid chamber 3 is limited by a wall 13 which is connected to the fluid inlet 5 and has a corresponding cut-out for receiving the same. The fluid inlet 5 is arranged preferably centrally in the wall 13 such that the fluid chamber 3 is in fluid communication with the fluid inlet 5. The fluid inlet 5 is in turn connected with its proximal end to an appropriate fluid pump or similar fluid pumping device of a surgical system.

The temperature control electrodes 11 and 11' are connected via electrical connections 15 and 15' to an HF generator 17 which transmits a high-frequency current to the temperature control electrodes 11 and 11' and which in particular is part of an HF surgical device. To prevent a short-circuit between the two temperature control electrodes, they are arranged at a distance a from each other. Spacers 19, which are in particular embedded in the electrodes 11 and 11' and prevent them from bumping against each other, are provided to ensure the distance a between the two electrodes 11 and 11'.

The spacers may be, for example, annular elements which are formed from a ceramic or a plastic material. As shown in FIG. 1, in the present embodiment a total of three spacers 19 are provided which extend segment-like between the temperature control electrodes 11 and 11' in sections in the axial direction A.

The temperature control electrodes 11 and 11' are formed from a conductive material and extend preferably over the entire length L of the fluid chamber 3. Provided at the distal end 21 of the multifunctional instrument 1 is an instrument attachment 23 which engages in particular positively in the distal end of the cylindrical sheath 7 of the multifunctional instrument 1 and seals it tight. For this, a corresponding step 25 of the instrument attachment is in contact with the inner surface 27 of the sheath on one hand, and with the end face S of the sheath 7 on the other.

In the embodiment shown in FIG. 1, an active electrode 29 extends into the fluid chamber 3 which is configured as a tubular element. It extends beyond an end face S of the instrument attachment 23 and protrudes with its proximal end 33 into the fluid chamber 3. The active electrode 29 is preferably movably supported in the instrument attachment 23 in the axial direction A such that a distal end 31*b* of said active electrode 29 can extend more or less beyond the end face S of the instrument attachment 23. The active electrode 29 further has a fluid outlet port 31 configured as an axial through-hole which is in fluid communication at its proximal end 31*a* with the fluid chamber 3, and whose distal end 31*b* is configured as a nozzle for generating a water jet or for discharging vapor to an operating region. The (monopolar) active electrode 29 is connected to the HF generator 17 via an electrical connection 35. In this case, the electrical connection 35 is arranged separately from the electrical connections 15 and 15' of the temperature control electrodes 11 and 11'. It should be pointed out at this point that the HF generator can be connected via another connection 37 to a neutral electrode that is not illustrated and which serves to feed back a current introduced into a patient by the monopolar active electrode 29.

In the embodiment shown in FIG. 1, the multifunctional instrument 1 comprises a further fluid outlet port 39 which is arranged eccentrically to the active electrode 29 in an axial direction in the instrument attachment 23. On the side directed towards the fluid chamber 3, the fluid outlet port 39 has a valve unit 41 which is illustrated here, by way of example, as a passive ball valve which opens or closes the fluid outlet port 39 as a function of a pressure prevailing in said fluid chamber 3. For example, the valve unit 41 may be configured such that the valve opens at a low pressure prevailing in the fluid chamber 3, in particular if the fluid present therein has been evaporated, and closes at higher pressures, i.e. if the fluid is present in liquid form.

If a high-frequency alternating current is applied to the temperature control electrodes 11 and 11', the current between the electrodes 11 and 11' is transmitted via the fluid located in the fluid chamber 3, which fluid was previously introduced into said fluid chamber 3 through the fluid inlet 5 at a specific flow rate. The temperature of the fluid located in the fluid chamber 3 can be determined without additional sensors by means of the preset flow rate and the wattage supplied to the temperature control electrodes. In this case, the temperature difference corresponds to the quotient from the energy supplied and the heat capacity: $\Delta T = \Delta E/(c*m)$. In this way, the fluid located in the fluid chamber 3 can be warmed, heated or even evaporated. Consequently, the temperature of the fluid located in the fluid chamber 3 can be controlled or regulated according to the application.

The ratio of the diameter of the fluid outlet ports 31 and 39 is preferably such that the fluid outlet port 31, centrally configured in the active electrode 29, preferably has a smaller diameter than the eccentric second fluid outlet port 39. Thus, while the first fluid outlet port 31, for example, has a diameter of approx. 50-500 μm, the second fluid outlet port 39 may have a correspondingly larger diameter.

Figure 2:
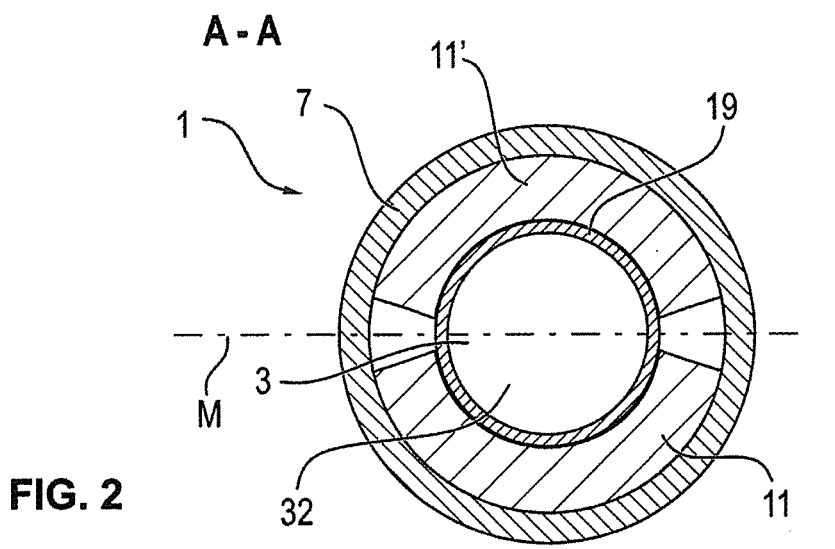
FIG. 2 is a sectional view of the multifunctional instrument of FIG. 1 along a section line A.

FIG. 2 shows a sectional view of the multifunctional instrument 1 along the section line A (see FIG. 1). The section runs through the sheath 7, the first temperature control electrode 11, the spacer 19, the fluid chamber 3 and through the second opposing temperature control electrode 11'. As is apparent from FIG. 2, the sheath 7 of the multifunctional instrument 1 is essentially cylindrical. It is preferably formed from a flexible material such that the multifunctional instrument can be used as a laparoscopic or endoscopic instrument for minimally invasive surgery.

The two temperature control electrodes 11 and 11' are configured identically and are essentially arranged so as to be laterally reversed in respect of a central plane M of the multifunctional instrument. In other words, they are arranged at the same height in the axial direction A while in the radial direction they are offset by 180° in relation to each other. Both temperature control electrodes 11 and 11' are essentially C-shaped or half-shell-shaped such that a circular spacer 19 can positively engage on both inner surfaces of the temperature control electrodes 11, 11'. The spacer 19 ensures that an insulation gap is maintained between the temperature control electrodes 11, 11'.

Figure 3:
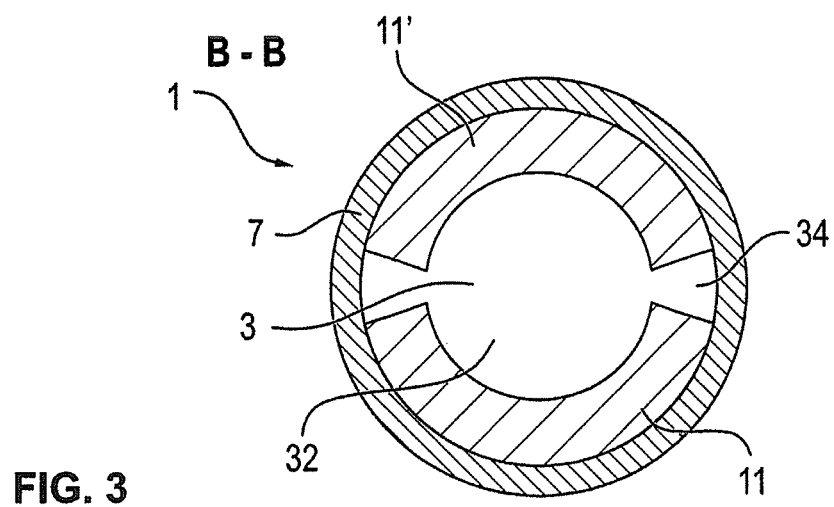
FIG. 3 is a sectional view of the multifunctional instrument of FIG. 1 along a section line B.

FIG. 3 shows a sectional view along the sectional plane B illustrated in FIG. 1. Consequently, the section runs through the sheath 7, the two temperature control electrodes 11 and 11' and through the fluid chamber 3. FIG. 3 makes it clear that the fluid chamber 3 comprises both an inner region 32, concentrically surrounded by the temperature control electrodes 11, 11', and also outer regions 34, each of which are formed between circumferential end sections of the temperature control electrodes 11, 11', said end sections being spaced apart from each other. Incidentally, the eccentric second fluid outlet port 39 can communicate with the fluid chamber 3 via a radial outer region 34.

Figure 4:
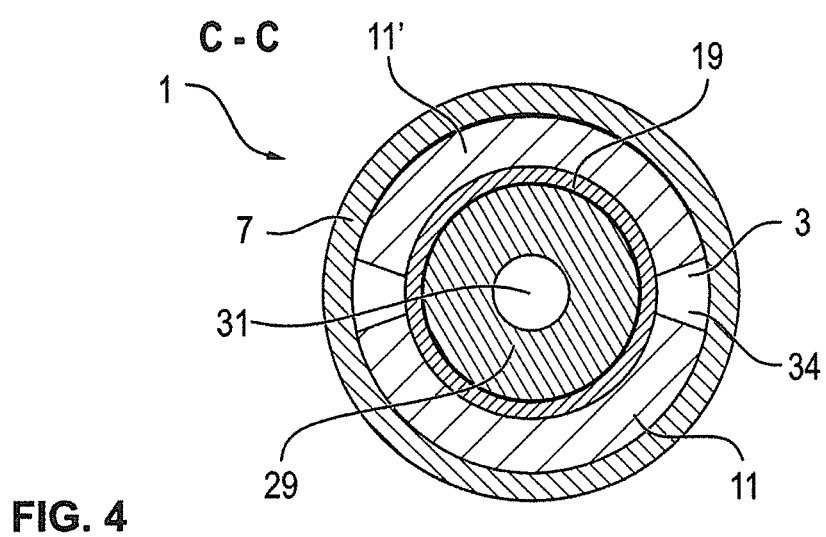
FIG. 4 is a sectional view of the multifunctional instrument of FIG. 1 along a section line C.

FIG. 4 shows another sectional view along a sectional plane C through the multifunctional instrument 1 (see FIG. 1). The sectional plane C extends in this case through the sheath 7, the two temperature control electrodes 11 and 11', through a spacer 19 and through the tubular active electrode 29.

FIG. 4 also makes it clear that the spacer 19 has a larger diameter than the remaining spacers 19 in the region of the active electrode 29. Incidentally, the fluid outlet port 31 in the active electrode 29 has a diameter which essentially corresponds to the inner diameter of the inner region 32 which forms an inner cylindrical fluid chamber channel and which forms between the two temperature control electrodes 11 and 11' with the help of spacers 19 (see also FIG. 1).

Figure 5:
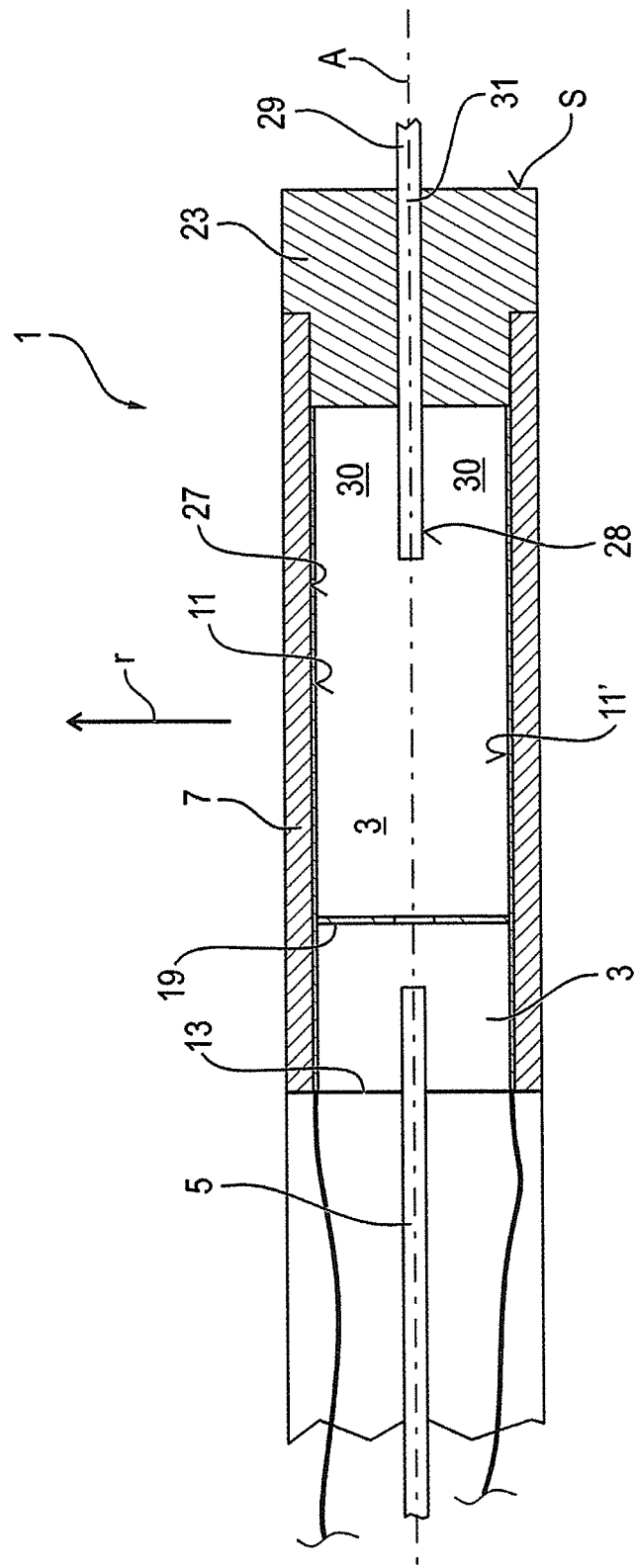
FIG. 5 is a schematic sectional view of a multifunctional instrument according to a further embodiment of the present invention.

FIG. 5 shows yet another embodiment in which the multifunctional instrument 1 essentially has flat temperature control electrodes 11 and 11' which may be formed, for example, of stainless steel. The temperature control electrodes 11 and 11' are attached to the inner surface 27 of the sheath 7 in the form of a thin layer of material. In particular, it may be provided that a segment-like division of the temperature control electrodes 11 and 11' is provided along the axial direction A of the multifunctional instrument to prevent the electrode from breaking in the event of the flexible sheath 7 bending.

To prevent a short-circuit between the temperature control electrodes 11 and 11' during kinking of the sheath 7, a spacer 19, for example of a ceramic material or similar insulation material, may also be provided between the electrodes in this embodiment. It is clear that the spacer 19 must be configured in such a way that it does not block a fluid which flows out of the fluid inlet 5 into the fluid chamber 3 and to the fluid outlet port 31. In the example shown, a fluid outlet port 31 can also be configured as a central through-hole in an active electrode 29 which extends beyond an end face S of an instrument attachment 23.

Other than in the embodiment shown in FIG. 1, the existing diameter of the active electrode 29 is, however, clearly smaller than the diameter of the fluid chamber 3 in a radial direction r of the multifunctional instrument 1. In this way, a fluid collection space 30 is formed between the inner wall (inner surface 27) of the fluid chamber 3 and the outer wall 28 of the active electrode 29 extending into the fluid chamber 3 which fluid collection space can prevent non-evaporated fluid from entering the fluid outlet port 31.

Overall, embodiments disclosed herein create an advantageous multifunctional instrument which, on one hand, can generate a focused water jet and is simultaneously capable of warming the fluid used therefor by means of an HF current. This warming may take place up to evaporation of the fluid, the HF current being used for this flowing not via the patient but rather exclusively via the connections 15, 15' inside the instrument. This is therefore a circuit which is separate from the patient circuit and which operates the temperature control device. It should be pointed out at this point that in principle the temperature control device can also be operated inductively.

Furthermore, embodiments disclosed herein render it possible use a single multifunctional instrument to mechanically treat or inject biological tissue with the help of a water jet. In this connection, it is possible at the same time to produce a coagulation effect using a heated fluid by applying an HF current to the active electrode. The temperature of the water can be determined in a particularly advantageous manner without additional sensors using the flow rate known to the HF surgical device and the wattage supplied to the temperature control electrodes.

In addition, the vapor generated in the fluid chamber 3 can produce a superficial, thermal effect with low penetration depth in order to devitalize the treated tissue over a large area. To do this, vapor generated by the temperature control electrodes 11 and 11' in the fluid chamber 3 is supplied via the fluid outlet port 31 and/or 39 or via further fluid outlet ports to an operating area, it being possible at the same time to apply an HF current to the active electrode 29. In this case, voltages of far less than 4500 V, in particular of less than 1000 V and in particular of less than 500 V are used. Unlike with conventional APC coagulation, it is possible in this manner to avoid carbonization effects of the tissue and neuromuscular stimulations as well as any negative effect on peripheral devices due to an applied high voltage.

Moreover, embodiments of the multifunctional instrument disclosed herein can also be used with a metal tip in the region of the distal end of the active electrode 29 as a classic, HF surgical cutting or coagulating instrument. As a result of the vapor generator unit in the region of the fluid chamber 3, the voltages for HF cutting or coagulating can in this case be significantly lower, at below 500 V, than with conventional APC or spray coagulation.

Heating of the fluid present in the fluid chamber 3 is accomplished by introducing the high-frequency alternating current into the temperature control electrodes 11, 11'. From there, the alternating current continues to flow into the conductive fluid located in the fluid chamber 3 which flows through said chamber. The liquid in the fluid chamber warms up due to the electrical resistance.

All electrically conductive materials which are resistant to salt water during the instrument's period of use may be considered as the electrode material. The period of use is frequently only a few hours as these are typically disposable instruments which are disposed of after a single use. Stainless steel, conductive ceramics or conductive plastics are particularly suitable for this purpose. The fluid chamber 3 is in fluid communication with one or a plurality of nozzles 39, 31 at their distal end which can both produce a jet of fluid and also through which vapor can be discharged. Depending on the nozzle geometry and the fluid pressure, the jet of fluid can have different shapes, in particular diameters, and directions for different applications. The arrangement of a plurality of separate or interlinked fluid chambers 3 which may in turn be assigned one or a plurality of fluid outlet ports is also conceivable.

The whole multifunctional instrument is preferably cylindrical in construction, that is the sheath 7 in particular, such that it is possible to use it as a laparoscopic instrument with an outer diameter, for example, of 5 mm to 10 mm or as an endoscopic probe with an outer diameter of approx. 3 mm to 1.5 mm. Here, however, a mechanically flexible construction is advantageous so that the multifunctional instrument according to embodiments disclosed herein can follow bends inside an endoscope. This can be accomplished in that the conductive temperature control electrodes are manufactured from a segmented or a fabric-like material, this possibly being a thin film or a conductive coating which is attached to the inner surface 27 of the sheath 7.

What is claimed as new and desired to be protected by Letters Patent of the United States is:

1. A multifunctional instrument for HF surgical treatment of tissue, the multifunctional instrument comprising:
   at least one fluid chamber for receiving a fluid;
   a temperature control device communicating with the at least one fluid chamber for warming, heating or evaporating the fluid present in said at least one fluid chamber;
   a temperature controller for controlling the temperature of the fluid present in the at least one fluid chamber; and
   at least one fluid outlet port arranged in an active electrode configured as a hollow conductor and at a distal end of the multifunctional instrument and communicating with the at least one fluid chamber,
   wherein the active electrode protrudes beyond a distal end of a sheath of the multifunctional instrument and extends into the at least one fluid chamber, and a diameter of the at least one fluid chamber is greater than a diameter of the active electrode,
   wherein the at least one fluid outlet port, at a proximal end, is fluidly connected to the at least one fluid chamber and, at a distal end, is configured as a nozzle for generating a water jet or for dispensing a vapor, and
   wherein the multifunctional instrument is configured to dispense the water jet, for cutting tissue, from the at least one fluid outlet port.

2. The multifunctional instrument of claim 1, wherein the temperature control device comprises at least two temperature control electrodes arranged at a distance from each other which, at least in certain areas, form a wall of the at least one fluid chamber.

3. The multifunctional instrument of claim 2, wherein the temperature control electrodes have a radial gap between them which is determined in particular by at least one preferably annular-shaped spacer.

4. The multifunctional instrument of claim 2, wherein the temperature control electrodes are attached on an inner surface of a sheath, which is in particular cylindrical and flexible, and are preferably configured in the form of a coating, film or other thin material layer.

5. The multifunctional instrument of claim 1, wherein, for controlling/regulating the fluid temperature, the temperature controller adjusts the wattage supplied to the temperature control device, in particular to the temperature control electrodes, as a function of a specified fluid flow rate.

6. The multifunctional instrument of claim 1, wherein the active electrode and the temperature control electrodes are equipped with separate connections to the supply cable of a high-frequency current.

7. The multifunctional instrument of claim 1, wherein the distal end of the active electrode is configured as a cutting tool for mechanically cutting tissue and in particular has a cutting edge.

8. The multifunctional instrument of claim 1, further comprising at least one further fluid outlet port provided at a distal end of the instrument, said port communicating with the at least one fluid chamber or with at least one other fluid chamber.

9. The multifunctional instrument of claim 8, wherein the at least one further fluid outlet port is configured as a nozzle-type axial through-hole in an instrument attachment connected to the sheath at the distal end of the instrument.

10. The multifunctional instrument of claim 9, wherein the active electrode is arranged essentially centrally in the instrument attachment in an axial direction and in particular is movably supported therein.

11. The multifunctional instrument of claim 1, wherein one or a plurality of the fluid outlet ports is or are provided with a valve unit which is configured in particular as a passive ball or active piezo valve.

12. The multifunctional instrument of claim 11, wherein the valve unit is arranged at a proximal end of the fluid outlet port, in particular at a proximal end of the instrument attachment.

13. An HF surgical system, having at least one HF generator for generating a high-frequency treatment current as well as for generating a temperature control current, and having a multifunctional instrument according to claim 1.

* * * * *